(12) United States Patent
Okuda et al.

(10) Patent No.: US 8,226,784 B2
(45) Date of Patent: Jul. 24, 2012

(54) METHOD OF FORMING LAMINATED BODY AND METHOD OF MANUFACTURING SENSOR ELEMENT

(75) Inventors: Yuji Okuda, Niwa (JP); Shin Murai, Kitanagoya (JP)

(73) Assignees: NGK Insulators, Ltd., Nagoya (JP); NGK Optoceramics Co., Ltd., Komaki (JP); NGK Printer Ceramics Co., Ltd., Komaki (JP)

( * ) Notice: Subject to any disclaimer, the term of this patent is extended or adjusted under 35 U.S.C. 154(b) by 40 days.

(21) Appl. No.: 12/358,450

(22) Filed: Jan. 23, 2009

(65) Prior Publication Data

US 2009/0188620 A1    Jul. 30, 2009

(30) Foreign Application Priority Data

Jan. 28, 2008    (JP) ................. 2008-016629

(51) Int. Cl.
- C03B 29/00    (2006.01)
- B29C 65/00    (2006.01)

(52) U.S. Cl. .............. 156/89.12; 156/89.11; 156/277
(58) Field of Classification Search .......... 156/89.12, 156/277

See application file for complete search history.

(56) References Cited

U.S. PATENT DOCUMENTS

| | | | |
|---|---|---|---|
| 5,787,866 A * | 8/1998 | Sugiyama et al. | 123/672 |
| 6,451,187 B1 * | 9/2002 | Suzuki et al. | 204/426 |
| 6,721,163 B2 * | 4/2004 | Iwase et al. | 361/301.4 |
| 6,797,138 B1 * | 9/2004 | Detwiler et al. | 204/427 |
| 2004/0144476 A1 | 7/2004 | Fukuta et al. | |
| 2004/0158971 A1 * | 8/2004 | Kawashima | 29/592.1 |
| 2004/0217098 A1 * | 11/2004 | Polikarpus et al. | 219/209 |
| 2005/0274615 A1 * | 12/2005 | Naito et al. | 204/424 |
| 2007/0214865 A1 * | 9/2007 | Nakae et al. | 73/19.01 |
| 2009/0084673 A1 * | 4/2009 | Ogata et al. | 204/243.1 |

FOREIGN PATENT DOCUMENTS

| | | |
|---|---|---|
| JP | 08-271476 A1 | 10/1996 |
| JP | 2002-76626 | 3/2002 |
| JP | 2002-340848 A1 | 11/2002 |
| JP | 2004-037473 A1 | 2/2004 |
| JP | 2004-117099 A1 | 4/2004 |
| JP | 2005310554 A * | 11/2005 |
| JP | 2006-284223 A1 | 10/2006 |
| JP | 2007-024670 A1 | 2/2007 |
| JP | 2007-085946 A1 | 4/2007 |
| WO | WO 2007004500 A1 * | 1/2007 |

* cited by examiner

Primary Examiner — Philip Tucker
Assistant Examiner — Alex Efta
(74) Attorney, Agent, or Firm — Burr & Brown

(57) ABSTRACT

A method of forming a laminated body includes a first lamination step of forming a preceding lamination sheet which is substantially treated as one green sheet initially by laminating and bonding at least two green sheets together out of a plurality of green sheets; a printing step of printing a predetermined pattern on the preceding lamination sheet and at least one non-preceding lamination sheet which is a not used for forming the preceding lamination sheet; and a second lamination step of laminating and bonding the preceding lamination sheet and non-preceding lamination sheet, on which the predetermined pattern is printed in the printing step, in a predetermined order.

4 Claims, 8 Drawing Sheets

F I G . 4
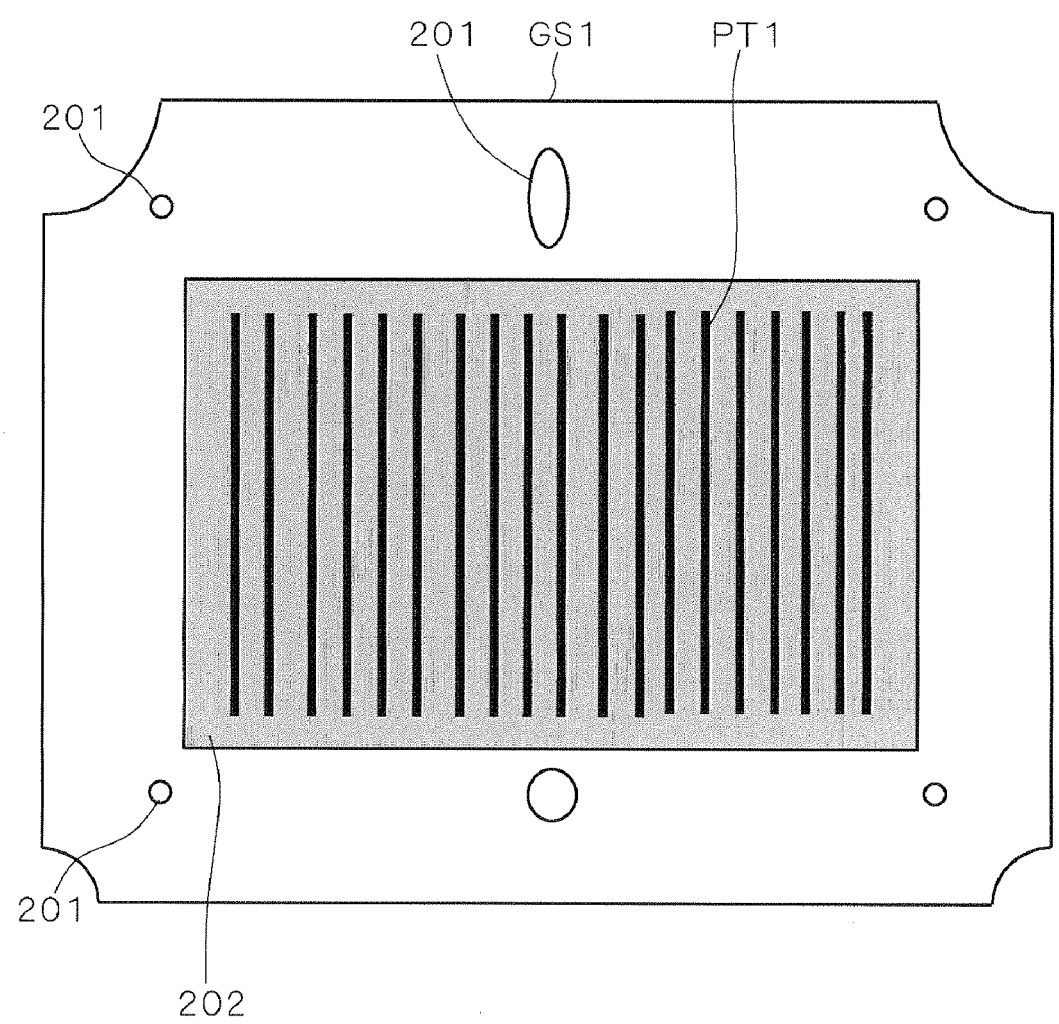

METHOD OF FORMING LAMINATED BODY AND METHOD OF MANUFACTURING SENSOR ELEMENT

BACKGROUND OF THE INVENTION

1. Field of the Invention

The present invention relates to a method of forming a laminated body by laminating a ceramics green sheet, and more specifically, to a method of forming a laminated body preferable for manufacturing a gas sensor for measuring a predetermined gas concentration in a measurement gas.

2. Description of the Background Art

Conventionally, various measuring devices have been used for determining a concentration of a desired gas component in a measurement gas. A known device of measuring a NOx concentration in a measurement gas such as a combustion gas, for example, is a sensor having a Pt-containing electrode and a Rh-containing electrode formed on an oxygen ion conductive solid electrolyte, such as zirconia ($ZrO_2$) (see Japanese Patent Application Laid-Open No. 8-271476 and Japanese Patent Application Laid-Open No. 2004-37473, for example).

A gas sensor as recited in Japanese Patent Application Laid-Open No. 8-271476 or Japanese Patent Application Laid-Open No. 2004-37473 is manufactured by cutting and burning a laminated body formed by laminating and integrating a plurality of ceramics green sheets (hereinafter also referred to as merely "green sheets") including zirconia, which is an oxygen ion conductive solid electrolyte, as a ceramics component, a predetermined circuit pattern (hereinafter also referred to as merely a "pattern") being formed on each of the plurality of ceramics green sheets.

The circuit pattern is formed by a printing method using a predetermined printing paste. When laminating a plurality of relatively thick green sheets with a thickness of a few hundred μm, the plurality of green sheets may be laminated with a bonding paste printed (applied) previously thereon. As a result, printing (and drying thereafter) may be performed more than once on a green sheet composing each layer of the laminated body. The green sheet is normally deformed every time printing is done. Thus the problem arises that the layered accuracy is lowered if using the green sheet on which printing is performed many times (allowing laminating failure exceeding the acceptable range), causing the yield deterioration in manufacturing a gas sensor or the like.

The laminated green sheet is integrated by heating and applying a pressure with an oil-hydraulic press, where an establishment of conditions is needed to laminate with high accuracy and stability.

SUMMARY OF THE INVENTION

The present invention relates to a method of forming a laminated body by laminating a ceramics green sheet, and more specifically, to a method of forming a laminated body preferable for manufacturing a gas sensor for measuring a predetermined gas concentration in a measurement gas.

A method of forming a laminated body according to the invention includes the following steps of: (a) forming a preceding lamination sheet which is substantially treated as one ceramics green sheet by laminating and bonding at least two ceramics green sheets out of a plurality of ceramics green sheets; (b) printing a predetermined pattern on the preceding lamination sheet and at least one non-preceding lamination sheet which is a ceramics green sheet not used for forming the preceding lamination sheet out of the plurality of ceramics green sheets; (c) laminating and bonding the preceding lamination sheet and non-preceding lamination sheet, on which the predetermined pattern is printed in the step (b), in a predetermined order.

The present invention makes it possible to form the laminated body with high accuracy by previously laminating and bonding in advance a ceramics green sheet which is easily deformed in subsequent steps.

Also the present invention is directed to a method of manufacturing a sensor element including steps of forming a laminated body by the method of forming the laminated body by the above described method of the present invention.

It is therefore an object of the present invention to provide a method of forming a laminated body in which green sheets are laminated with preferable lamination accuracy.

These and other objects, features, aspects and advantages of the present invention will become more apparent from the following detailed description of the present invention when taken in conjunction with the accompanying drawings.

BRIEF DESCRIPTION OF THE DRAWINGS

FIG. 4 is a schematic view for showing one example of a green sheet GS1 on which an adhesive 202 consisted of a bonding paste is applied after forming a pattern PT1.

DETAILED DESCRIPTION OF THE INVENTION

<Gas Sensor>

Figure 1:
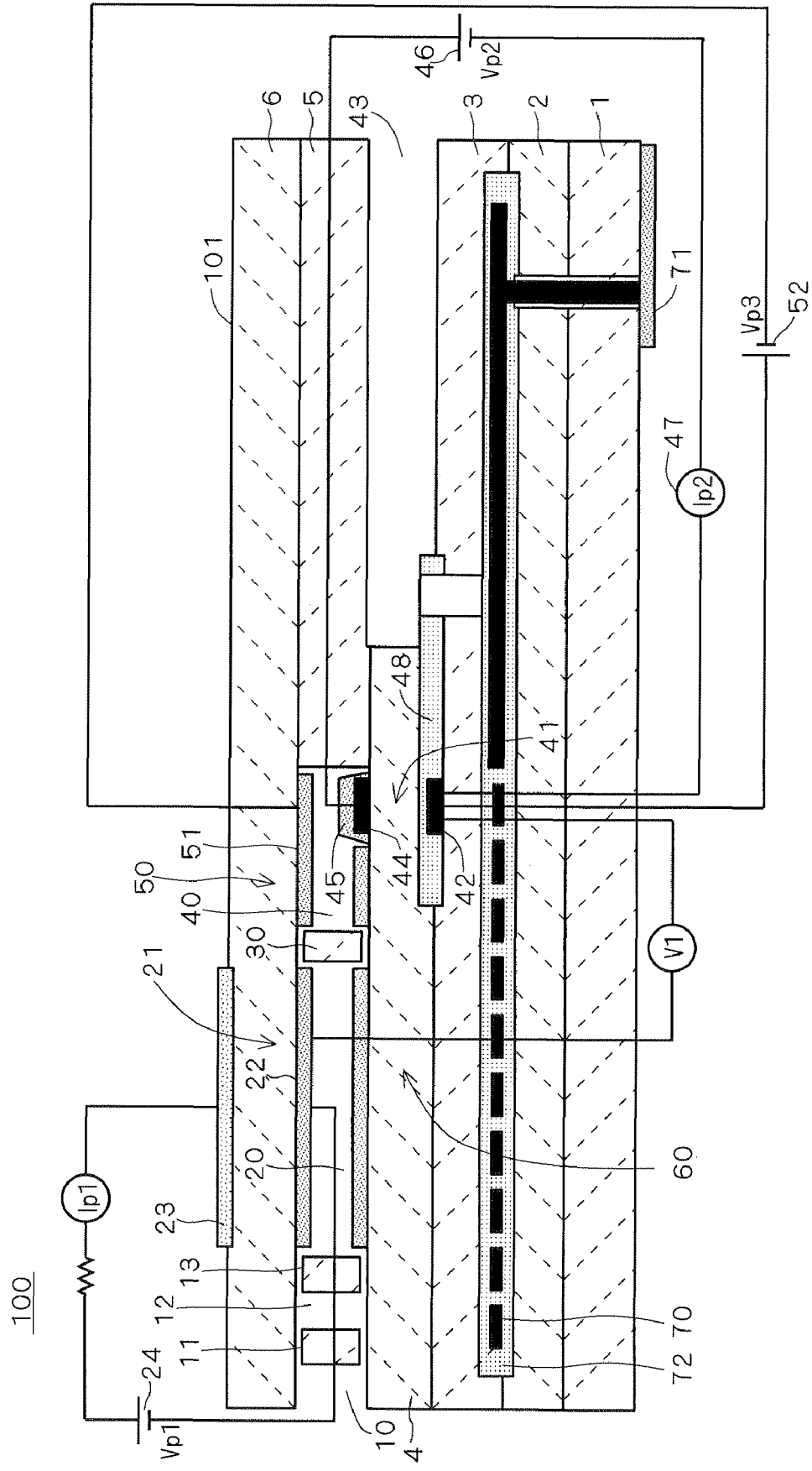
FIG. 1 is an outline sectional schematic view for showing a structure of a gas sensor 100 according to a preferred embodiment of the invention.

FIG. 1 is an outline sectional schematic view for showing a structure of a gas sensor 100 according to a preferred embodiment of the invention. The gas sensor 100 detects a predetermined gas component in a gas which is an object of measurement (a measurement gas), and further, measures a concentration thereof The present embodiment will be described taking an example where the gas sensor 100 is a NOx sensor detecting nitrogen oxide (NOx) as an object component. The gas sensor 100 includes a sensor element 101 consisting of an oxygen ion conductive solid electrolyte such as zirconia ($ZrO_2$).

Specifically, the sensor element 101 includes a structure laminating a first substrate layer 1, a second substrate layer 2, a third substrate layer 3, a first solid electrolyte layer 4, a spacer layer 5, and a second solid electrolyte layer 6 in this order from a bottom seen in FIG. 1, each of the layers consisting of an oxygen ion conductive solid electrolyte.

A gas inlet 10, a first diffusion control part 11, a buffer space 12, a second diffusion control part 13, a first internal space 20, a third diffusion control part 30 and a second internal space 40 are adjacently formed in this order and in communication with one another between a lower surface of the second solid electrolyte layer 6 and an upper surface of the first solid electrolyte layer 4 at a tip of the sensor element 101. The gas inlet 10, the buffer space 12, the first internal space 20 and the second internal space 40 are provided by hollowing out the spacer layer 5, which is a space with an upper portion sectioned by the lower surface of the second solid electrolyte layer 6, an lower portion sectioned by the upper surface of the first solid electrolyte layer 4, and a side portion sectioned by a side surface of the spacer layer 5. Each of the first diffusion control part 11, the second diffusion control part 13 and the third diffusion control part 30 is provided as two horizontally long (an opening has a longitudinal direction in a direction perpendicular to FIG. 1) slits arranged one above the other. The part from the gas inlet 10 to the second internal space 40 is also referred to as a gas distribution part.

A reference gas inlet space 43 is provided between an upper surface of the third substrate layer 3 and a lower surface of the spacer layer 5 at a position which is farther from the tip than the gas distribution part is. The reference gas inlet space 43 is a space with an upper portion sectioned by the lower surface of the spacer layer 5, a lower portion sectioned by the upper surface of the third substrate layer 3, and a side portion sectioned by a side surface of the first solid electrolyte layer 4. For example, air is introduced to the reference gas inlet space 43 as a reference gas.

The gas inlet 10 is open to outside, and a measurement gas is brought into the sensor element 101 from outside therethrough.

The first diffusion control part 11 provides a predetermined diffusion resistance to the measurement gas brought into from the gas inlet 10.

The buffer space 12 is provided in order to counteract concentration fluctuation of the measurement gas caused by pressure fluctuation (pulsation of exhaust pressure if a measurement gas is an emission gas of automobiles) of the measurement gas outside.

The second diffusion control part 13 provides a predetermined diffusion resistance to the measurement gas brought into the second diffusion control part 13 from the buffer space 12.

The first internal space 20 is provided as a space for controlling oxygen partial pressure in the measurement gas introduced through the second diffusion control part 13. The oxygen partial pressure is controlled by operating a main pump cell 21.

The main pump cell 21 is an electrochemical pump cell composed of an inside pump electrode 22 provided on an almost whole surface in a part of the lower surface of the second solid electrolyte layer 6 facing the first internal space 20, an outside pump electrode 23 provided in a region corresponding to the inside pump electrode 22 on an upper surface of the second solid electrolyte to be exposed outside, and a part of the second solid electrolyte layer 6 interposed between those electrodes. The inside pump electrode 22 and the outside pump electrode 23 are formed as porous cermet electrodes (e.g. cermet electrodes of Pt and $ZrO_2$ including Au by 1%) which are oblong in a plane view. Further, the inside pump electrode 22 is formed using material in which reduction ability to an NO component in the measurement gas is weakened, or material without reduction ability.

The main pump cell 21 is provided with a variable power source 24 outside the sensor element 101. The variable power source 24 applies a desired pump voltage Vp1 between the inside pump electrode 22 and the outside pump electrode 23 to flow pump current Ip1 in a positive direction or a negative direction between the outside pump electrode 23 and the inside pump electrode 22, allowing to pump out oxygen in the first internal space 20 to an outside space or to pump in oxygen in the outside space into the first internal space 20.

The third diffusion control part 30 provides a predetermined diffusion resistance to the measurement gas brought into the second internal space 40 from the first internal space 20.

The second internal space 40 is provided as a space for performing a process to measure concentration of nitrogen oxide (NOx) in the measurement gas introduced through the third diffusion control part 30.

A NOx concentration can be measured by operating a measuring pump cell 41. The measuring pump cell 41 is an electrochemical pump cell composed of a reference electrode 42 between the upper surface of the third substrate layer 3 and the first solid electrolyte layer 4, a measuring electrode 44 provided on the upper surface of the first solid electrolyte layer 4 facing the second internal space 40, spaced apart from the third diffusion control part 30, and the first solid electrolyte layer 4. Each of the reference electrode 42 and the measuring electrode 44 is a porous cermet electrode which is substantially oblong in a plane view. The reference electrode 42 is surrounded by an air induction layer 48 consisted of porous alumina and leading to a reference gas introduction space. The measuring electrode 44 is composed of metal obtained by resolving NOx which is a measurement gas component, and of porous cermet consisted of zirconia. Therefore, the measuring electrode 44 serves as a NOx reduction catalyst for resolving NOx in an atmosphere of the second internal space 40.

Moreover, the measuring electrode 44 is covered with a fourth diffusion control part 45. The fourth diffusion control part 45 is a film consisted of alumina, and functions to limit the amount of NOx flowing into the measuring electrode 44.

The measuring pump cell 41 is provided with a DC power source 46 applying a pump voltage Vp2 which is a fixed voltage between the measuring electrode 44 and the reference electrode 42 to resolve NOx. As a result, oxygen is generated in an atmosphere inside the second internal space 40, and then the oxygen is pumped out to the reference gas inlet space 43. A pump current Ip2 allowed to flow by the operation of the measuring pump cell 41 is detected by an ammeter 47.

Also, with respect to the measurement gas introduced into the second internal space 40 through the third diffusion control part 30, oxygen partial pressure is previously controlled in the first internal space 20, and thereafter, the oxygen partial pressure is further controlled by an auxiliary pump cell 50. Accordingly, the gas sensor 100 can perform the measurement of a NOx concentration with high accuracy.

The auxiliary pump cell 50 is an electrochemical pump cell composed of an auxiliary pump electrode 51 provided on substantially whole surface in a part of the lower surface of the second solid electrolyte 6 facing the second internal space 40, the second solid electrolyte 6, the spacer layer 5, the first solid electrolyte 4 and the reference electrode 42.

Similarly to the inside pump electrode 22, the auxiliary pump electrode 51 is formed using material in which reduction ability to an NO component in the measurement gas is weakened, or material without reduction ability.

The auxiliary pump cell 50 is provided with a DC power source 52 outside the sensor element 101. The DC power source 52 applies a fixed voltage Vp3 between the auxiliary pump electrode 51 and the reference electrode 42 to pump out oxygen in an atmosphere inside the second internal space 40 into the reference gas inlet space 43.

Moreover, the sensor element 101 includes an oxygen partial pressure detecting sensor cell 60 which is an electrochemical pump cell composed of the inside pump electrode 22, the reference electrode 42, the second solid electrolyte layer 6, the spacer layer 5 and the first solid electrolyte layer 4.

The oxygen partial pressure detecting sensor cell 60 detects oxygen partial pressure in the atmosphere of the first internal space 20 based on a electromotive force V1 generated between the inside pump electrode 22 and the reference electrode 42 which is caused by the difference of oxygen concentration between the atmosphere of the first internal space 20 and a reference gas (air) of the reference gas inlet space 43. The detected oxygen partial pressure is used for feedback controlling the variable power source 24. Specifically, a pump voltage applied to the main pump cell 21 is controlled so as to set oxygen partial pressure in the atmosphere of the first internal space 20 at a predetermined value which is lower enough to control oxygen partial pressure in the second internal space 40.

Moreover, the sensor element 101 includes a heater 70 formed to be interposed between the second substrate layer 2 and the third substrate layer 3 from above and below. The heater 70 generates heat by power feeding from outside through a heater electrode 71 provided on a lower surface of the first substrate layer 1. Heat generation by the heater 70 allows to enhance oxygen ion conductivity of solid electrolyte composing the sensor element 101. The heater 70 is buried in the whole area from the first internal space 20 to the second internal space 40 so that a predetermined area of the sensor element 101 is heated and kept warm at a predetermined temperature. A heater insulating layer 72 consisted of alumina or the like is formed on an upper surface and a lower surface of the heater 70 in order to obtain electronic insulation between the second substrate layer 2 and the third substrate layer 3 (hereinafter, the heater 70, the heater electrode 71 and the heater insulating layer 72 are also collectively referred to as a heater part).

In the gas sensor 100 having the above described structure, the measurement gas is provided with the measuring pump cell 41, with oxygen partial pressure constantly maintained at fixed low value (a value substantially unaffecting the measurement of NOx) by operating the main pump cell 21 and the auxiliary pump cell 50. Accordingly, a pump current is substantially proportional to the reduced NOx concentration, the pump current flowing in the measuring pump cell 41 by pumping out oxygen generated by a reduction of NOx.

<Manufacturing Sensor Element>

Next, a method of manufacturing the sensor element 101 according to the present embodiment will be described.

In the present embodiment, the sensor element 101 is manufactured by forming a laminated body consisted of green sheets including oxygen ion conductive solid electrolyte such as zirconia as a ceramics component, cutting and burning the laminated body. Roughly mentioned, the laminated body is formed by the following; forming a penetrating portion on a plurality of green sheets, each of which corresponds to each layer of the sensor element 101, by punching or the like to form an internal space, printing a predetermined pattern in accordance with a laminating position, and laminating the plurality of green sheets one another after printing and applying a bonding paste thereon as an adhesive. A publicly known screen printing process is available for printing a pattern and an adhesive. Also, a publicly known drying process is available for a drying process after printing.

When the sensor element 101 consists of zirconia, it is a preferable example to use a green sheet including a binder of butyral system and a solvent of alcohol system. In this case, it is further preferable to use a green sheet with almost 5 to 10 parts by weight of a binder and almost 0 to 5 parts by weight of a solvent to 100 parts by weight of the green sheet.

A bonding paste used is mainly consisted of ceramics substantially similar to a ceramics component of the green sheet, and includes a binder and a solvent. When the sensor element 101 is consisted of zirconia, it is preferable to use the bonding paste including zirconia as a ceramics component, butyral system as a binder and alcohol system as a solvent.

In the above case, it is preferable that the bonding paste includes from greater than or equal to 12 to less than or equal to 16 parts by weight of a binder to 100 parts by weight of the bonding paste. Further, it is more preferable to use the bonding paste including 14 parts by weight of a binder to 100 parts by weight of the bonding paste. If the weight of a binder is less than the above range, viscosity of the bonding paste is not large enough to obtain sufficient adhesion. Therefore, the problem arises that adhesion of the green sheets are unstable and not maintained, for example, even if the green sheets are bonded to each other, they are peeled off right away or the like. If the weight of a binder is small, viscosity tends not to be large even though a temperature is increased. On the other hand, if the weight of a binder is greater than the above range, deformation of the green sheets by laminating becomes large, causing a problem to easily produce a crack in the laminated body. The inventors of the present invention have confirmed that the adhesion of the green sheets in laminating gets stable when using a binder with low polymerization degree, and the less stable the adhesion gets, the higher the polymerization degree is.

Components of the bonding paste are not limited to the above, other material may be used as long as the adhesion and the lamination of the green sheets are performed preferably and unless an adverse effect is imposed on characteristics of the sensor element 101.

It will be described below, making the case where the sensor element 101 consisted of six layers shown in FIG. 1 as an example. In this case, six green sheets are prepared to correspond to the first substrate layer 1, the second substrate layer 2, the third substrate layer 3, the first solid electrolyte layer 4, the spacer layer 5 and the second solid electrolyte layer 6, respectively.

Figure 2:
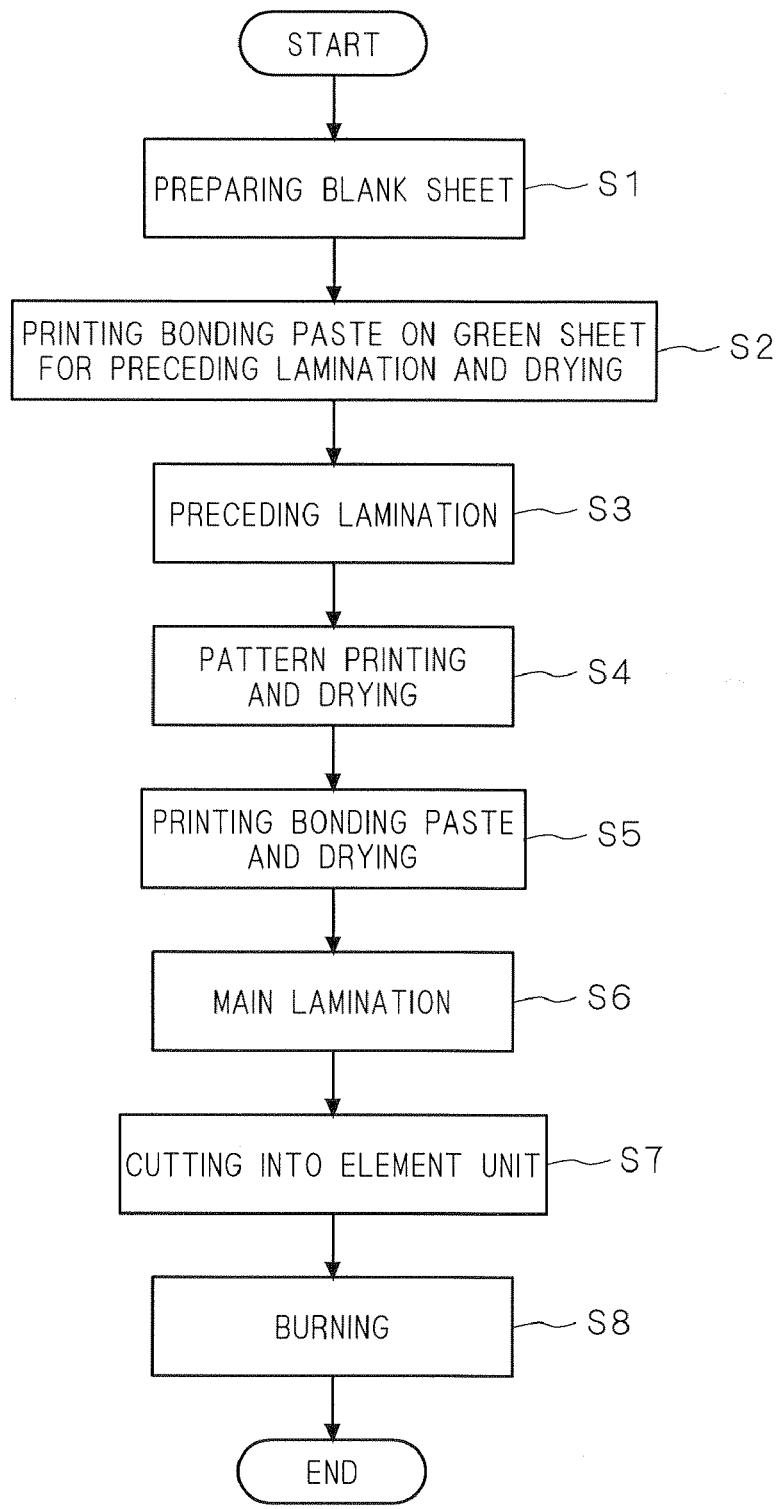
FIG. 2 illustrates a flow of a process in manufacturing a sensor element 101.
Figure 3:
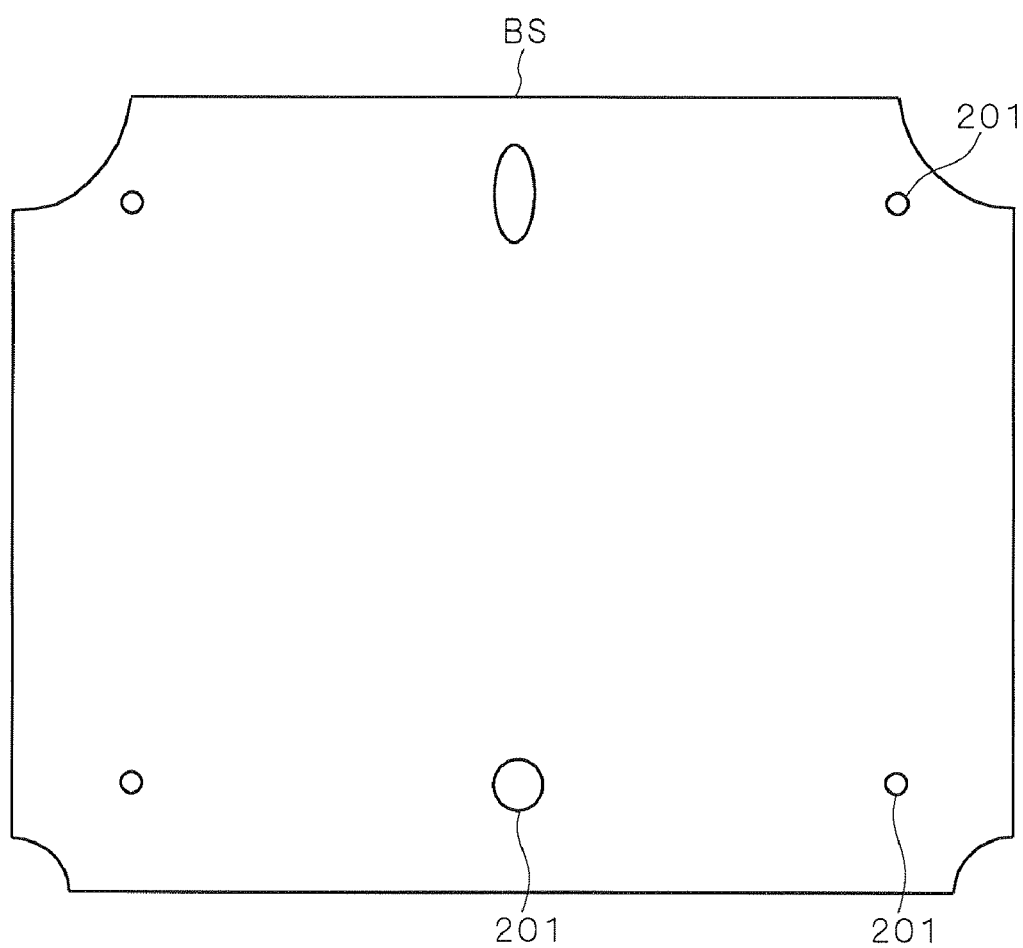
FIG. 3 illustrates a blank sheet BS.

FIG. 2 illustrates a flow of a process in manufacturing a sensor element 101. Also, FIG. 3 illustrates a blank sheet BS which is a green sheet before printing a pattern. When manufacturing the sensor element 101, at first, six blank sheets BS are prepared to correspond to each layer of the sensor element 101 (a step S1). The green sheets for composing a layer corresponding to an internal space are previously provided with penetrating portions corresponding to the internal space by punching with a punching machine or the like, which is not shown in FIG. 3. It should be noted that thickness of each blank sheet BS corresponding to each layer of the sensor element 101 is not necessarily same with each other.

Furthermore, a plurality of sheet holes 201 are provided on the blank sheet BS, as shown in FIG. 3. The sheet holes 201 are through holes previously provided on an edge region not contributing to the composition of the sensor element 101 in the blank sheet BS (a region made redundant after the lamination). These sheet holes 201 are used for positioning or fixing in printing a pattern or laminating a green sheet. In addition, they may be used as a marker (reference position) for evaluating deformation of sheets. It should be noted that position and shape of the sheet holes 201 are not limited to what is shown in FIG. 1.

After preparing the blank sheet BS, a bonding paste as an adhesive is printed and dried so as to laminate and bond green sheets corresponding to predetermined successive two layers of the sensor element 101 (a step S2).

Subsequently, these two zirconia sheets are preceded to laminate (a step S3). These two green sheets which are preceded to laminate are treated altogether substantially as one green sheet in later steps. Hereinafter, a laminated body obtained by the above preceding lamination is called a preceding lamination sheet. Also, a green sheet which is not used for the preceding lamination is called a non-preceding lamination sheet. Drying condition and laminating condition of the adhesive in the preceding lamination are same as a main lamination described below (a lamination for obtaining a laminated body corresponding to a whole gas sensor is referred to as a main lamination in order to distinguish from the preceding lamination), which is not described here.

In the sensor element 101 according to the present embodiment, a green sheet corresponding to the first substrate layer 1 and a green sheet corresponding to the second substrate layer 2 are targets of the preceding lamination. These (i.e., blank) green sheets are selected as targets of the preceding lamination so as to obtain preferable lamination accuracy in the resulting lamination of a laminated body. The inventors of the invention have confirmed that if the same pattern formed on these two green sheets is printed on both surfaces of one green sheet (in particular, when the heater part is printed on one green sheet, hereinafter referred to as a case of a single sheet), the number of times of printing and drying to form necessary pattern is larger than other four non-preceding lamination sheets so that deformation volume of a single sheet is remarkably great, being unable to obtain preferable lamination (details will be described later). Therefore, the preceding lamination sheet in which two green sheets are previously laminated and bonded together is used for forming the heater part in the present embodiment so as to suppress an extent of the deformation. That is, similarly to a single sheet, the number of times of printing and drying which are necessary for the preceding lamination sheet is still larger than the number of times of printing and drying for the green sheets composing other four layers, but the deformation volume of the sheet by printing and drying in the preceding lamination sheet is smaller than in the single sheet even if the same printing is performed. Therefore the more preferable lamination is obtained rather than the single sheet. It should be noted that the number of green sheets composing the preceding lamination sheet is not limited to two, but more green sheets may be preceded to laminate to form the preceding lamination sheet according to a condition of a pattern printing or the like on a laminated body to be formed.

After obtaining the preceding lamination sheet, subsequently, a pattern printing and a drying process are performed on the preceding lamination sheet and the non-preceding lamination sheet (a step S4). The pattern printing on the non-preceding lamination sheet or the like may precede to form the preceding lamination sheet, or performed at the same time as forming the preceding lamination sheet.

After the pattern printing is finished, a printing and drying process of a bonding paste for laminating and bonding the preceding lamination sheet and the non-preceding lamination sheet. (a step S5). The inventors have confirmed that it is preferable to perform the drying process with from greater than or equal to 80% to less than or equal to 90% of a weight decreasing amount of a solvent in the bonding paste (details will be described later).

FIG. 4 is a schematic view for showing one example of a green sheet GS1 on which an adhesive 202 consisted of a bonding paste is applied after forming a pattern PT1. In the present embodiment, the pattern PT1 for a plurality of the sensor elements 101 is printed on each of the green sheets so as to obtain a plurality of the sensor elements 101 from a single laminated body. Further, the pattern PT1 formed on each of the green sheets depends on the layer of the sensor element 101 which each green sheet composes. As described above, a green sheet of a layer composing a side surface of the internal space is provided with a penetrating portion at a predetermined position, which is not shown in FIG. 4.

Subsequently, the main lamination is performed in which the green sheets applied the adhesive are laminated in a predetermined order and crimped with a predetermined temperature and a pressure condition to obtain a single laminated body (a step S6).

More specifically, the main lamination and the aforementioned preceding lamination are performed by laminating the green sheets which are objects of lamination, and holding the laminated green sheets onto a predetermined lamination jig not shown by positioning in accordance with the sheet holes 201, and further, heating and pressurizing the green sheets together with the lamination jig by a lamination machine such as a known oil-hydraulic press machine. The inventors have found out a preferable range of heating and pressurizing in lamination (details will be described later).

The period of heating and pressurizing depends on the lamination machine which is used, however, it may be good enough to determine appropriate conditions so as to obtain a preferable lamination. Furthermore, it is not essential to equalize the conditions of the preceding lamination and the main lamination, but the process may be performed with different conditions for each of the preceding lamination and the main lamination.

After obtaining the laminated body as described above, the laminated body is cut into each unit (referred to as a divided body) of the sensor elements 101 (a step S7). The divided body which is obtained is burned with a predetermined condition to generate the sensor element 101 (a step S8).

<Effect of Preceding Lamination>

Next, details will be described on effects of the preceding lamination of a predetermined two green sheets, i.e. the effect of suppressing deformation of the green sheet when manufacturing the sensor element 101. As is the above described case, it will be described making the case of the preceding lamination of the green sheets composing the first substrate layer 1 and the second substrate layer 2 as an example.

Figure 5:
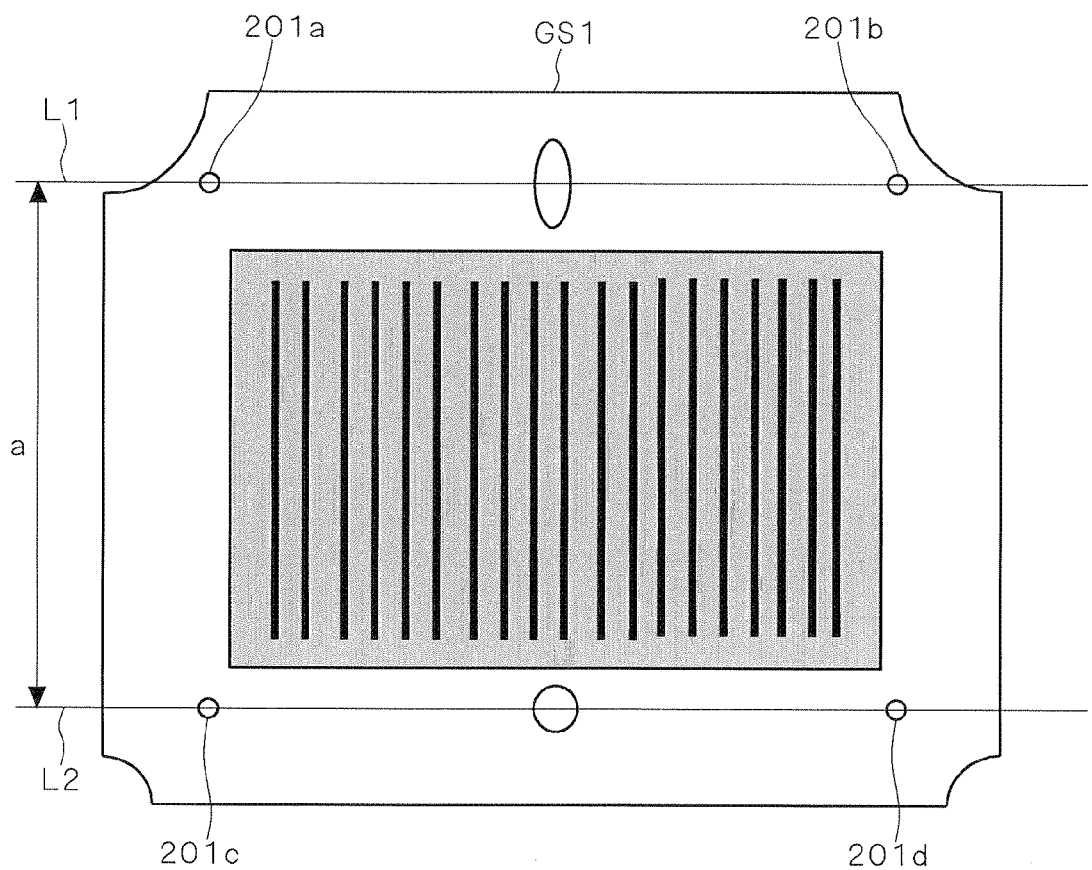
FIG. 5 is a view for illustrating one example of a method of measuring a deformation volume of the green sheet GS1 to the blank sheet BS.

FIG. 5 is a view for illustrating one example of a method of measuring a deformation volume of the green sheet GS1 to the blank sheet BS. In the present embodiment, a distance a between a line L1 connecting a sheet hole 201a with a sheet hole 201b and a line L2 connecting a sheet hole 201c with a sheet hole 201d, which are shown in FIG. 5, is measured in the blank sheet BS before printing and after a pattern printing and drying, and then the variation volume of the measured value is calculated as the deformation volume.

Table 1 shows the deformation volume of the deformation caused between the green sheet before printing and the green sheet after printing when composing the sensor element 101 using the green sheet with a sheet size of 150 mm by 114 mm including zirconia as an oxygen ion conductive solid electrolyte component. Table 1 also shows the deformation volume of the green sheet composing other layers in addition to the deformation volume of the preceding lamination sheet and the single sheet.

TABLE 1

| Green Sheet | Deformation Volume (mm) |
|---|---|
| Single Sheet | −0.50 |
| Preceding Lamination Sheet | −0.20 |
| Sheet Composing Third Substrate Layer | −0.25 |
| Sheet Composing First Solid Electrolyte Layer | −0.25 |
| Sheet Composing Spacer Layer | −0.25 |
| Sheet Composing Second Solid Electrolyte Layer | −0.30 |

As shown in Table 1, while the deformation volume of the single sheet in which a pattern corresponding to the first substrate layer 1 and the second substrate layer 2 is printed on one green sheet is −0.50 mm, the deformation volume of the preceding lamination sheet is shown to be −0.20 mm. On the other hand, the deformation volume of the non-preceding lamination sheet is −0.30 mm even for the largest absolute value. Therefore, the difference of the deformation volume with other layers can be suppressed by forming a layer, which used to be formed with the single sheet, with the preceding lamination sheet. That is, dislocation of positioning becomes smaller in laminating by adopting the preceding lamination so that the lamination with high accuracy can be carried out.

It should be noted that the measurement method of the deformation volume is not limited to the above method. The measurement method is particularly not limited as long as it is a method which is able to measure quantitatively sheet deformation caused by pattern printing and drying.

<Evaluation of Lamination State>

There are various methods to evaluate if the lamination is performed preferably for the laminated body obtained by the above described steps. In the present embodiment, the lamination state is evaluated by the following method.

1) Peel Test: which is to examine if the green sheets composing each layer of the laminated body is firmly adhered to each other and not peeled off, by pulling an edge portion of the laminated body with a predetermined force. If peeling arises, it is determined to be a lamination defect.

Figure 6:
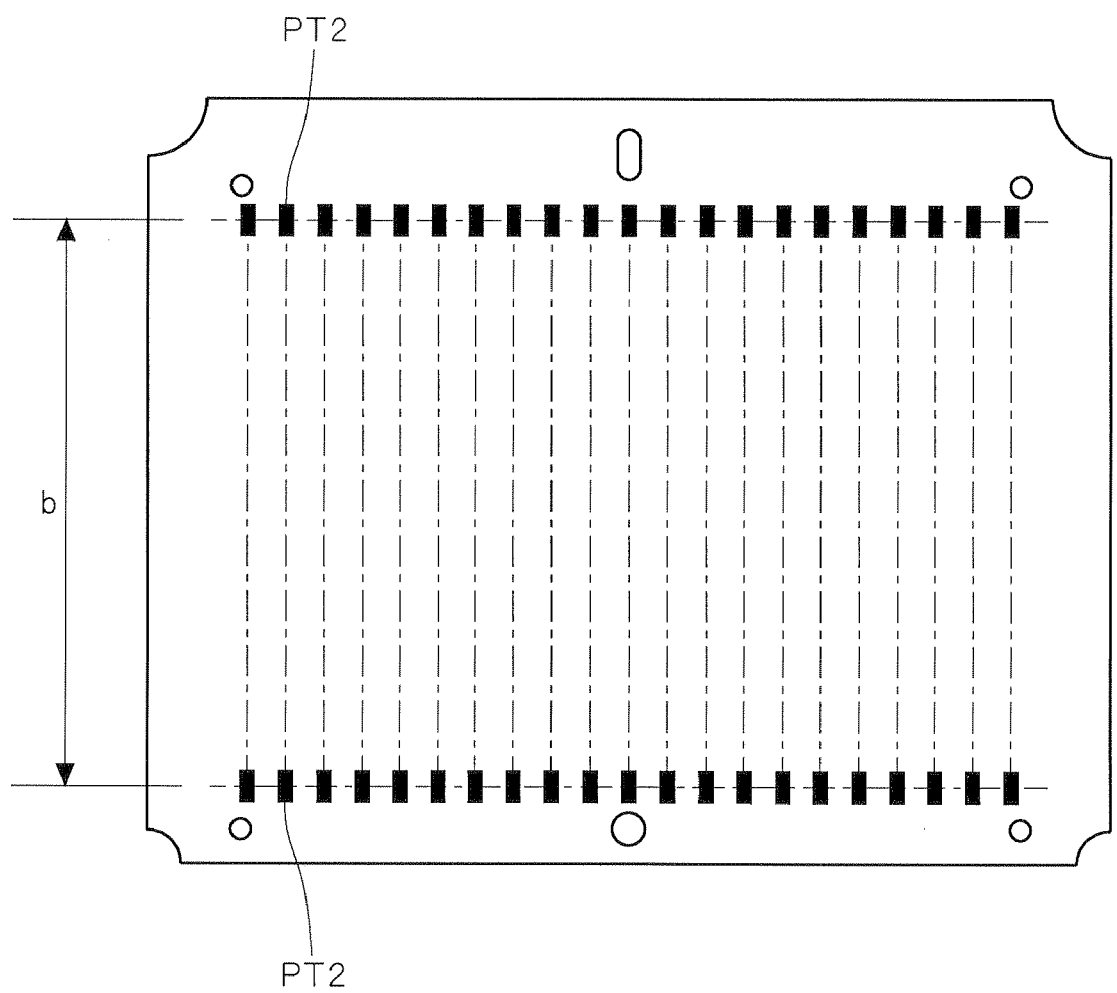
FIG. 6 is a schematic view of a pattern PT2 printed on a green sheet laminated on a top most surface of a laminated body.

2) Pattern Size Change Evaluation: which is performed to examine if change of a pattern size by the lamination is within an acceptable range. FIG. 6 is a schematic view of a pattern PT2 printed on a green sheet which is a target of the pattern size measurement and laminated on a top most surface of a laminated body. The pattern PT2 is measured before and after the lamination by an image microscope. A distance b shown in FIG. 6 (size of a surface pattern) is measured to determine a deformation volume before and after the lamination. If the deformation volume exceeds a range of a predetermined reference value, it is determined to be a lamination defect (a sheet deformation evaluation before and after the lamination).

3) Crack Test: which is to confirm whether or not there is a crack by cutting the formed laminated body and checking a cross section of the cut laminated body by a microscope or the like. If there is a crack, it is determined to be a lamination defect.

Figure 7A:
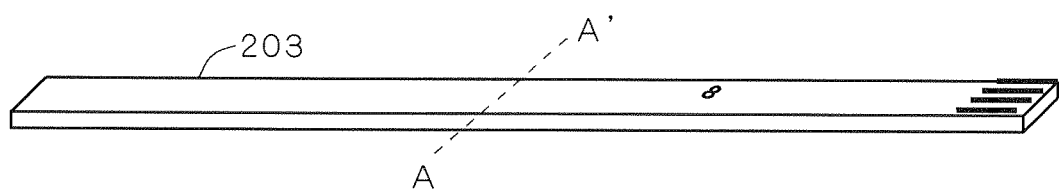
FIGS. 7A and 7B are views for illustrating one example of an evaluation method of laminating dislocation.
Figure 7B:
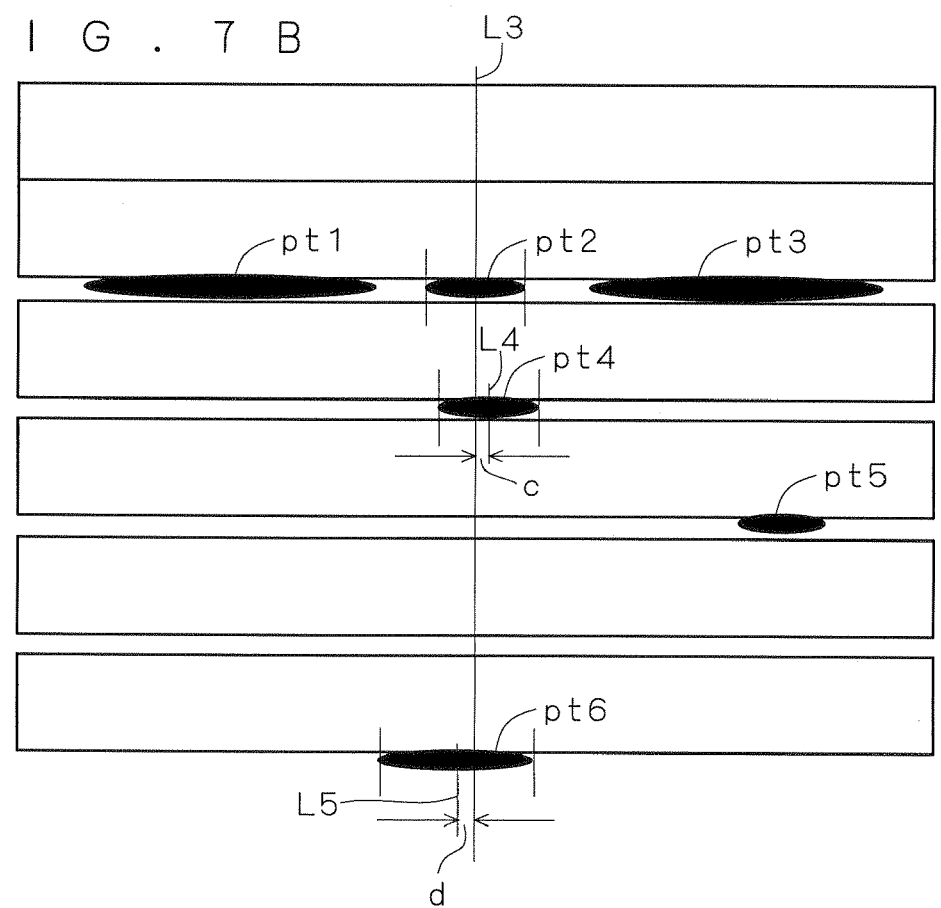

4) Laminating Dislocation Evaluation: which is to evaluate the extent of dislocation for each layer in a direction perpendicular to a lamination direction. If a volume of laminating dislocation exceeds a range of a predetermined reference value, it is determined to be lamination defect. FIGS. 7A and 7B are views for illustrating one example of an evaluation method of laminating dislocation. FIG. 7A is a perspective view for showing an unburned laminated body 203 (becoming the sensor element 101 by being burned), which is an evaluation target, seen from a back surface side (a side of the first substrate layer 1). In this method, the laminated body 203 is cut vertically in a longitudinal direction at a position A-A', and a cross section thereof is evaluated. FIG. 7B is a cross sectional view of A-A' in the laminated body 203 shown in FIG. 7A. According to this method, the targets of the laminating dislocation are patterns pt2, pt4 and pt6 located substantially near the center in a horizontal direction in patterns pt1 to pt6 formed on each layer shown in FIG. 7B. More specifically, each of a center position in a horizontal direction (a position of a line L3) of the pattern pt2 formed on the second substrate layer 2, a center position in a horizontal direction (a position of a line L4) of the pattern pt4 formed on the third substrate layer 3 and a center position in a horizontal direction (a position of a line L5) of the pattern pt6 formed on the second solid electrolyte layer 6 is measured by a microscope. If a distance c and a distance d between a horizontal position of the line L3 and horizontal positions of other lines exceed a predetermined range, it is determined to be a lamination defect.

The evaluation methods of lamination state as described above are only examples, and so do not restrict to determine by other evaluation methods.

<Condition of Heating and Pressurizing in Laminating>

Next, the condition of a temperature and a pressure (condition of heating and pressurizing) in the main lamination and the preceding lamination will be described.

Table 2 shows a quality of the lamination state when forming the laminated body by changing temperature and pressure (gauge pressure). Specifically, Table 2 shows whether the results of the above described peel test and pattern size change evaluation fulfill a predetermined reference. In the result shown in Table 2, it is determined to be a lamination defect in the case where the deformation volume exceeds 0.3 mm in the pattern size change evaluation. Noted that a cross mark in Table shows that the lamination state is not preferable and a white circle shows that the lamination state is preferable.

TABLE 2

| Gauge Pressure (kgf/cm$^2$) | 70° C. | 80° C. | 90° C. | 100° C. | 110° C. |
|---|---|---|---|---|---|
| 25  | X | X | X | X | X |
| 40  | X | X | X | ○ | X |
| 55  | X | X | ○ | ○ | X |
| 70  | X | ○ | ○ | ○ | X |
| 85  | ○ | ○ | ○ | ○ | X |
| 100 | ○ | ○ | ○ | ○ | X |
| 115 | ○ | ○ | ○ | X | X |
| 130 | ○ | ○ | X | X | X |

As shown in Table 2, when the temperature reaches 110° C., a preferable laminated body cannot be obtained regardless of the gauge pressure. When the temperature is less than or equal to 70° C., the adhesion between the green sheets in the laminated body is getting weaker. The upper limit and the lower limit of the gauge pressure to obtain a preferable laminated body vary linearly to the temperature.

Figure 8:
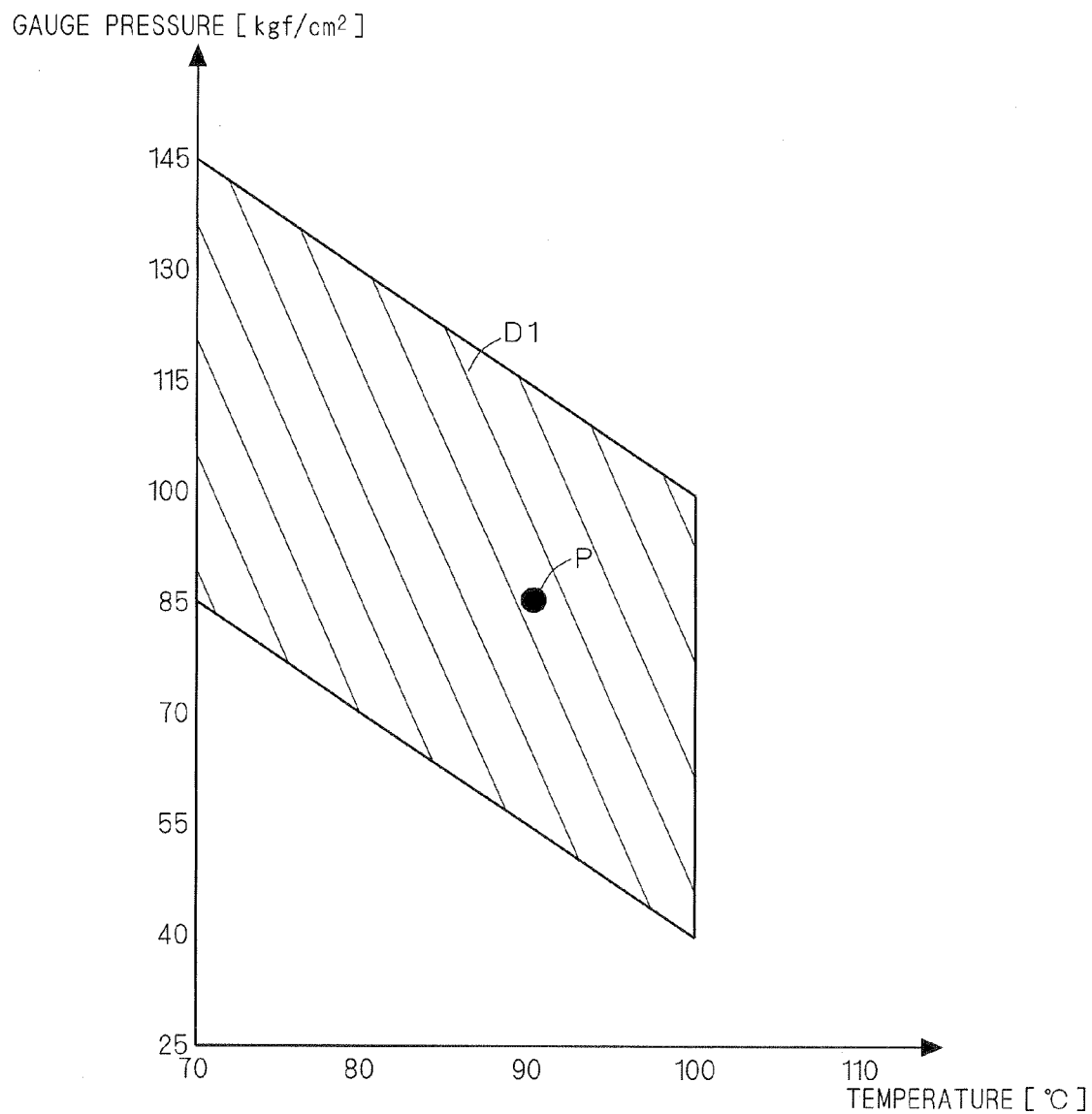
FIG. 8 is a plane view of a temperature and a pressure (T-p plane) showing a range for forming a preferable laminated body.

FIG. 8 is a plane view of the temperature and the pressure (T-p plane) for showing a range forming a preferable laminated body based on the result shown in Table 2. That is, in the present embodiment, it is preferable that the value of the temperature and the pressure in laminating belongs to a region D1 defined by the following equations (1) to (4) in the T-p plane.

Numerical Expression 1

$$p \geq -(3/2)T + 190 \quad (1)$$

$$p \leq -(3/2)T+250 \quad (2)$$

$$T \geq 70 \quad (3)$$

$$T \leq 100 \quad (4)$$

It is more preferable to perform the main lamination with the temperature and the pressure shown by a point P in FIG. 8, i.e. with the temperature of 90° C. and the gauge pressure of 85 kgf/cm².

The result in a range of the temperature of less than or equal to 80° C. and the gauge pressure of greater than or equal to 130 kgf/cm² shown in FIG. 8 is not shown in Table 2.

<Condition of Bonding Paste>

Next, the condition of a binder weight in the bonding paste will be described.

Table 3 shows a quality of the lamination state when forming the laminated body by changing the binder weight in the bonding paste. Specifically, Table 3 shows whether the results of the above described peel test, pattern size change evaluation and crack test fulfill a predetermined reference. Table 3 shows the result when varying a ratio of the binder weight to 100 parts by weight of the bonding paste. The evaluation is made under the condition of the temperature of 90° C. and the gauge pressure of 85 kgf/cm². It has been confirmed that the lamination state does not change abruptly even if the above temperature and pressure are changed within the region D1 shown in FIG. 8.

TABLE 3

| | Binder Weight | | | | | | | | |
|---|---|---|---|---|---|---|---|---|---|
| | 10% | 11% | 12% | 13% | 14% | 15% | 16% | 17% | 18% |
| Lamination State | X | X | ○ | ○ | ○ | ○ | ○ | X | X |

According to the result of Table 3, it is preferable to include from greater than or equal to 12 to less than or equal to 16 parts by weight of the binder to 100 parts by weight of the bonding paste. Further, it is more preferable to use the bonding paste with the binder having 14 parts by weight to 100 parts by weight of the bonding paste. As described above, as a result, if the binder weight is less than the above range, sufficient adhesion cannot be obtained because viscosity of the bonding paste is not enough. On the other hand, if the binder weight is greater than the above range, deformation of a green sheet before and after the lamination becomes large so that a crack is easily generated.

<Drying Condition of Bonding Paste>

Subsequently, drying condition of the bonding paste will be described. If drying of the bonding paste is not enough when bonding and laminating a green sheet, sufficient adhesion in laminating the green sheets cannot be obtained. Insufficient drying here means that the flying amount of a solvent of the bonding paste in the air is small, which corresponds to that a weight decreasing amount of the solvent in drying is small. In contrast, if the flying amount of the solvent in the air is excessive, that is, if the weight decreasing rate of the solvent is too high, the binder is difficult to dissolve in the solvent when bonding the green sheets so that the adhesion between the green sheets is weakened.

Table 4 below shows a quality of the lamination state when manufacturing the laminated body with different weight decreasing amounts of the solvent of the bonding paste. The evaluation is made under the condition of the temperature of 90° C. and the gauge pressure of 85 kgf/cm². It has been confirmed that the lamination state does not change abruptly even if the above temperature and pressure are changed within the region D1 shown in FIG. 8. The weight decreasing amount of the solvent is controlled by adjusting time of drying performed after printing the bonding paste.

TABLE 4

| | Weight Decreasing Amount of Solvent | | | | | |
|---|---|---|---|---|---|---|
| | 75% | 80% | 85% | 90% | 95% | 100% |
| Lamination State | X | ○ | ○ | ○ | X | X |

According to the result of Table 4, the weight decreasing amount of the solvent of the binder in the bonding paste is preferably from greater than or equal to 80% to less than or equal to 90%, more preferably 85%.

As discussed above, according to the present embodiment, when composing a laminated body by laminating a plurality of green sheets on each of which a pattern is printed and an adhesive is applied, stable lamination with high accuracy can be performed by forming a laminated body by laminating a plurality of (at least two) the green sheets in advance to prepare a preceding lamination sheet treated in the same manner as a single sheet, instead of a green sheet where deformation volume is increased when a single sheet is provided for the lamination, thereby causing lamination defects. As a result, yield deterioration can be prevented by lamination defect when manufacturing a laminated body to be a sensor element of a gas sensor, for example.

A method of forming a laminated body includes a first lamination step of forming a preceding lamination sheet which is substantially treated as one green sheet initially by laminating and bonding at least two green sheets together out of a plurality of green sheets; a printing step of printing a predetermined pattern on the preceding lamination sheet and at least one non-preceding lamination sheet which is a not used for forming the preceding lamination sheet; and a second lamination step of laminating and bonding the preceding lamination sheet and non-preceding lamination sheet, on which the predetermined pattern is printed in the printing step, in a predetermined order.

While the invention has been shown and described in detail, the foregoing description is in all aspects illustrative and not restrictive. It is therefore understood that numerous modifications and variations can be devised without departing from the scope of the invention.

What is claimed is:

1. A method of manufacturing a gas sensor element comprising the steps of:
    (a) forming a preceding lamination sheet which is substantially treated and used as a single ceramics green sheet by laminating and bonding at least two blank ceramics green sheets together out of a plurality of ceramics green sheets, wherein said at least two blank ceramics green sheets have not been printed thereon, wherein said two blank ceramic sheets contact one another along their entire widths and lengths, respectively, and wherein the surfaces of said two blank ceramic sheets that contact one another have the same area;
    (b) printing a predetermined pattern on said preceding lamination sheet and at least one non-preceding lamination sheet which is a ceramics green sheet not used for forming said preceding lamination sheet out of said plurality of ceramics green sheets;

(c) laminating and bonding said preceding lamination sheet and said non-preceding lamination sheet, on which said predetermined pattern is printed in said step (b), in a predetermined order, wherein each of said steps (a) and (c) comprises the steps of:

(d) applying a bonding paste on said ceramics green sheets so as to bond each of said ceramics green sheets; and (e) drying said bonding paste applied in said step (d), wherein said bonding paste is dried so that a weight of a solvent is decreased in said bonding paste by greater or equal to 80% to less or equal to 90% in said step (e), wherein in step (c), laminating and bonding said preceding lamination sheet and said non-proceding lamination sheet is performed after step (e), wherein said predetermined pattern printed on said preceding lamination sheet is a heater pattern, and wherein said preceding lamination sheet defines an outermost surface of the gas sensor element.

2. The method according to claim 1, wherein said at least two ceramics green sheets used for forming said preceding lamination sheet are selected out of said plurality of ceramics green sheets so as that when said steps (a) and (b) are performed, the number of printing times for said preceding lamination sheet is larger than that for each ceramics green sheet to be non-preceding lamination sheet at that time.

3. The method according to claim 1, wherein a bonding paste used for bonding said ceramics green sheets in said steps (a) and (c) includes a binder from greater or equal to 12 to less or equal to 16 parts by weight to whole 100 parts by weight of said bonding paste.

4. The method according to claim 1, wherein a heating temperature and a pressure in at least one of said step (a) of forming said preceding lamination sheet or said step (c) of forming said laminated body is a temperature and a gauge pressure shown by a point (T, p) included in a region defined by the following equations in a plane T-p with a gauge pressure p kgf/cm$^2$ and a temperature T° C.;

$p \geq -(3/2)T+190$, $p \leq -(3/2)T+250$, $T \geq 70$, and $T \leq 100$.

* * * * *